US012657950B2

(12) United States Patent
Kong et al.

(10) Patent No.: US 12,657,950 B2
(45) Date of Patent: Jun. 16, 2026

(54) TASK-INDEPENDENT BRAINPRINT RECOGNITION METHOD BASED ON FEATURE DISENTANGLEMENT BY DECORRELATION

(71) Applicant: Hangzhou Dianzi University, Hangzhou City (CN)

(72) Inventors: Wanzeng Kong, Hangzhou City (CN); Xuanyu Jin, Hangzhou City (CN); Ni Li, Hangzhou City (CN); Jiajia Tang, Hangzhou City (CN)

(73) Assignee: Hangzhou Dianzi University, Hangzhou City (CN)

( * ) Notice: Subject to any disclaimer, the term of this patent is extended or adjusted under 35 U.S.C. 154(b) by 365 days.

(21) Appl. No.: 18/474,529

(22) Filed: Sep. 26, 2023

(65) Prior Publication Data

US 2024/0193986 A1     Jun. 13, 2024

(30) Foreign Application Priority Data

Dec. 8, 2022    (CN) .......................... 202211571546.3

(51) Int. Cl.
*G06V 40/10*          (2022.01)
*A61B 5/00*          (2006.01)
          (Continued)

(52) U.S. Cl.
CPC .............. *G06V 40/15* (2022.01); *A61B 5/117* (2013.01); *A61B 5/316* (2021.01); *A61B 5/725* (2013.01);
          (Continued)

(58) Field of Classification Search
CPC ...... G06V 40/15; G06V 10/62; G06V 10/764; G06V 10/774; G06V 10/776; G06V 10/82;
          (Continued)

(56) References Cited

U.S. PATENT DOCUMENTS

2018/0008145 A1*  1/2018  Freer .................... A61B 5/0006
2019/0113973 A1*  4/2019  Coleman ................ G06F 3/015
          (Continued)

*Primary Examiner* — Kathleen Y Dulaney
(74) *Attorney, Agent, or Firm* — Victor Cardona, Esq; Kevin Radigan, Esq.; Heslin Rothenberg Farley & Mesiti P.C.

(57)          ABSTRACT

The present disclosure provides a task-independent brainprint recognition method based on feature disentanglement by decorrelation. Existing methods fail to mine inherent identity information of a brain, leading to poor robustness of brainprint recognition in a scenario across tasks and difficulty of promotion thereof in practical use. The present disclosure firstly uses two branch networks to perform coarse-grained decomposition of identity information and task related information in an electroencephalogram (EEG). Secondly, in consideration of an influence of a task state on the identity information, a decorrelating method is employed such that the identity information and the task related information are independent as much as possible. Finally, a brainprint feature in the EEG is fully utilized for classification by adversarial self-supervision. The method of the present disclosure is good in performance and capable of realizing efficient task-independent brainprint recognition, and is a brainprint recognition method robustly useful in the real life.

20 Claims, 2 Drawing Sheets

(51) Int. Cl.

| | |
|---|---|
| *A61B 5/117* | (2016.01) |
| *A61B 5/316* | (2021.01) |
| *G06V 10/62* | (2022.01) |
| *G06V 10/764* | (2022.01) |
| *G06V 10/774* | (2022.01) |
| *G06V 10/776* | (2022.01) |
| *G06V 10/82* | (2022.01) |

(52) U.S. Cl.
CPC ............ *A61B 5/7257* (2013.01); *G06V 10/62* (2022.01); *G06V 10/764* (2022.01); *G06V 10/774* (2022.01); *G06V 10/776* (2022.01); *G06V 10/82* (2022.01)

(58) Field of Classification Search
CPC ......... A61B 5/117; A61B 5/316; A61B 5/725; A61B 5/7257; A61B 5/369; A61B 5/374; A61B 5/7235; A61B 5/7267; G06F 18/00; G06F 21/32; Y02D 10/00; G06N 3/08
USPC ................................. 382/115, 128, 190, 156
See application file for complete search history.

(56) References Cited

U.S. PATENT DOCUMENTS

| | | | |
|---|---|---|---|
| 2019/0332751 A1* | 10/2019 | Brady ................... | G06V 10/761 |
| 2020/0337625 A1* | 10/2020 | Aimone ............... | A61B 5/7267 |
| 2021/0193322 A1* | 6/2021 | Wischik ................ | G16H 50/20 |

* cited by examiner

TASK-INDEPENDENT BRAINPRINT RECOGNITION METHOD BASED ON FEATURE DISENTANGLEMENT BY DECORRELATION

CROSS REFERENCE TO RELATED APPLICATION

This patent application claims the benefit and priority of Chinese Patent Application No. 202211571546.3, filed with the China National Intellectual Property Administration on Dec. 8, 2022, the disclosure of which is hereby incorporated herein by reference in its entirety as part of the present application.

TECHNICAL FIELD

The present disclosure belongs to the field of electroencephalogram (EEG) signal recognition in the field of biometric feature recognition, and particularly relates to a task-independent brainprint recognition method based on feature disentanglement by decorrelation that is intended to obtain identity information independent of task information based on feature disentanglement by decorrelation and utilize a brainprint feature for identity recognition by adversarial self-supervision.

BACKGROUND

Biometric recognition is dependent on an individual feature and plays a vital role in an authentication system. While physical biometric recognition techniques such as face recognition and fingerprint recognition have been extensively applied to the real life, potential hazards of elaborate forgery or secret reproduction are still inevitable. In addition to physical biometric recognition, brain activity recorded by an electroencephalogram (EEG) is proposed as a new cognitive biometric feature, which meets a basic recognition requirement and referred to as "brainprint". Moreover, only a living individual can provide brain activity signals, and these signals are not controlled by a user. This means that the identity information of the user may not be leaked or stolen intentionally. Accordingly, an EEG-based biometric recognition technique can be used in applications with high security requirements.

In recent years, according to a type of task stimulus received by a subject, brainprint recognition may be roughly divided into four major categories: brainprint recognition based on a resting potential (RP), brainprint recognition based on a visual evoked potential (VEP), brainprint recognition based on movement imagery (MI), and brainprint recognition based on an event-related potential (ERP). These brainprint recognition categories still have some problems. Brainprint recognition based on an external stimulus requires that a subject has no corresponding physiological defects and can receive an external stimulus. Moreover, these brainprint recognition categories are directed at particular task stimuli, can be hardly promoted and used in the reality, and have limitations. Compared with existing methods, a task-independent brainprint recognition method based on feature disentanglement by decorrelation is proposed, which is intended to disentangle identity information and task information in an EEG and fully utilize a brainprint feature to realize highly robust brainprint recognition across tasks.

SUMMARY

In view of the shortcomings of the prior art, an objective of the present disclosure is to provide a task-independent brainprint recognition method based on feature disentanglement by decorrelation. The task-independent brainprint recognition method based on feature disentanglement by decorrelation is mainly intended to disentangle identity information and task information in an electroencephalogram, extract independent identity information, and fully utilize the identity information by adversarial self-supervision.

In a first aspect, the present disclosure provides a task-independent brainprint recognition method based on feature disentanglement by decorrelation, specifically including the following steps:

step 1, preprocessing original EEG data and establishing a data set;

step 2, establishing an EEG feature extraction network for extracting a multi-scale time-frequency-space feature of a brainprint, specifically including:

step 2-1, dividing each EEG sample into low-frequency, high-frequency, and full-frequency subsamples by a low frequency band, a high frequency band, and a full frequency band;

step 2-2, separately subjecting low-frequency, high-frequency, and full-frequency time-frequency features to two layers of one-dimensional time-domain convolutions and one layer of one-dimensional frequency-domain convolution having different kernel sizes to extract advanced time-frequency brainprint features of low-frequency, high-frequency, and full-frequency EEGs;

step 2-3, obtaining a time-frequency brainprint feature $$\{f_i \in \mathbb{R}^{n \times c}\}_{i=1}^3$$

of each EEG sample by extracting a time-domain brainprint feature and a frequency-domain brainprint feature, where $\mathbb{R}$ represents a set of real numbers, n represents a number of hidden layers, and c represents a number of EEG channels; and step 2-4, splicing the time-frequency brainprint features by frequency-domain dimensions to obtain a time-frequency feature $f_{ts} \in \mathbb{R}^{n \times c \times 3}$, then performing channel-wise and spatial convolutions on the time-frequency feature $f_{ts}$ with a two-dimensional convolution kernel of (c×3), and outputting the multi-scale time-frequency-space feature $f \in \mathbb{R}^n$ of the brainprint;

step 3, establishing a primary brainprint and task disentangling neural network model;

where the primary brainprint and task disentangling neural network model includes a primary brainprint disentangling neural network and a primary task disentangling neural network that are concurrent;

the primary brainprint disentangling neural network includes an EEG feature extraction network $G_f$ and an identity discriminator $C_f$; the EEG feature extraction network $G_f$ is configured to extract identity information, and is the EEG feature extraction network established in step 2; the identity discriminator $C_f$ is configured for identity recognition, and includes a main classifier C and an auxiliary classifier Cs that are concurrent; and the main classifier C and the auxiliary classifier Cs are both fully connected layers;

a loss function of the EEG feature extraction network $G_f$ is as follows:

$$\mathcal{L}_s = -\frac{1}{n}\sum_{i=1}^{m} \hat{P} \log C_f(G_f(x_i)) = -\frac{1}{n}\sum_{i=1}^{m} \hat{P} \log C_f(f) \quad (2)$$

where $\mathcal{L}_s$ represents the loss function; n represents a number of samples; m represents a number of subjects; and $\hat{P}$ represents a probability that input data $x_i$ belongs to subject m;

the primary task disentangling neural network includes an EEG feature extraction network $G_t$ and a task classifier $C_t$; the EEG feature extraction network $G_t$ is configured to extract task information, and is the EEG feature extraction network established in step 2; and the task classifier $C_t$ is configured for task discrimination, and is a fully connected layer;

step 4, training the primary brainprint and task disentangling neural network model training, specifically including:

step 4-1, establishing constraint conditions for the EEG feature extraction networks $G_f$ and $G_t$: decorrelating the identity information $S=G_f(x)$ and the task information $A=G_t(x)$, specifically including:

(1) splicing an original identity feature matrix S and an original task feature matrix A output by the EEG feature extraction networks $G_f$ and $G_t$ to obtain a new matrix $Q \in \mathbb{R}^{m_S \times m_Q}$, where $m_S$ represents a number of samples, and $m_Q$ represents feature dimensions; mapping the matrix Q to a high-dimensional reproducing kernel Hilbert space (RKHS), and determining a dependency relationship between any two vectors $q_i, q_j$ in the matrix Q by a Hilbert-Schmidt independence criterion (HSIC), where $i, j \in m_Q$; and calculating a Frobenius norm of a cross-covariance operator in the RKHS;

acquiring an independent representation for a kernel function by mapping original data to the RKHS, as shown below:

$$\mathcal{K}(x;) = \Sigma_i \alpha_i \varphi_i(x) \varphi_i(\cdot) = \left(\sqrt{\alpha_i}\, \varphi_i(x), \cdots \right)_{\mathcal{H}} \quad (3)$$

where $\mathcal{K}(\bullet, \bullet)$ represents a measurable symmetric positive definite kernel function; $\varphi$ represents a mapping function; $(\cdot)_{\mathcal{H}}$ represents a Hilbert space; and ai represents a feature value;

(2) detecting independence of the vectors $q_i, q_j$ by the HSIC after acquiring the kernel function;

for random variables $q_i, q_j$ and kernel functions $\mathcal{K}1$, $\mathcal{K}2$, defining the HSIC as:

$$HSIC^{\mathcal{K}1,\mathcal{K}2}(q_i, q_j) := \left\| C_{q_i,q_j}^{\mathcal{K}1,\mathcal{K}2} \right\|_F^2 \quad (4)$$

where $C^{\mathcal{K}1,\mathcal{K}2}$ represents the cross-covariance operator regarding the kernel functions $\mathcal{K}1$ and $\mathcal{K}2$ in the RKHS; $\|\bullet\|_F$ is the Frobenius norm; and there exists $HSIC^{\mathcal{K}1,\mathcal{K}2}(q_i, q_j) = 0 \Leftrightarrow q_i \perp q_j$, with $q_i$ being independent of $q_j$;

(3) optimizing the kernel function $\mathcal{K}(x, \bullet)$;

approximating the kernel function using random Fourier features (RFF) due to a high complexity of calculating the kernel function $\mathcal{K}(x, \bullet)$ in the Hilbert space, acquiring a dimension-reduced function by Fourier transform sampling to approximate the original kernel function, and capturing a nonlinear correlation of the two vectors $q_i, q_j$, specifically including:

mapping the vectors $q_i, q_j$ to a low-dimensional Euclidean space using the RFFs by the following formula (5), and obtaining an inner product after the mapping as an estimated value of the kernel function; performing linear calculation using the RFFs to remove the nonlinear correlation to realize statistical independence of the features;

expressing a random Fourier function space $\mathcal{H}_{RFF}$ as:

$$\mathcal{H}_{RFF} = \left\{ h\colon x \to 2\sqrt{2}\, \cos(\omega x + \phi) \,\middle|\, \omega \sim N(0, 1), \phi \sim U(0, 2\pi) \right\} \quad (5)$$

where h represents a random Fourier feature mapping function; $\omega$ represents sampling from a standard normal distribution $N(0,1)$; $\phi$ represents sampling from a uniform distribution $U(0,2\pi)$; and x represents the vectors $q_i, q_j$; and transforming the matrix Q into the RFFs by the formula (5) to approximate the kernel functions $\mathcal{K}(x, \bullet)$ of an identity feature and a task feature;

(4) detecting the independence;

assuming that there exist measurable spaces $\Omega_1$ and $\Omega_2$, where $(\mathcal{H}_1, \mathcal{K}_1)$ and $(\mathcal{H}_2, \mathcal{K}_2)$ represent the RKHSs in $\Omega_1$ and $\Omega_2$, and correspondingly, $\mathcal{K}_1$ and $\mathcal{K}_2$ are also measurable, and a unique cross-covariance operator $\Sigma_{XY}$ exists in a space from $\mathcal{H}_1$ to $\mathcal{H}_2$, deriving:

$$\langle g, \Sigma_{XY} f \rangle = Cov(f(X), g(Y)) = \mathbb{E}_{XY}[f(X)g(Y)] - \mathbb{E}_X[f(X)]\mathbb{E}_Y[g(Y)] \quad (6)$$

where $f(X) \in \mathcal{H}_1$, $g(Y) \in \mathcal{H}_2$, and $Cov(\bullet)$ represents a covariance matrix;

as shown in the Formula (6), the calculation of $\Sigma_{XY}$ is expanded to the calculation of the covariance matrix over the Euclidean space, and $f(X)$ and $g(Y)$ represent nonlinear kernel functions; due to $\Sigma_{XY}=0 \Leftrightarrow X \perp Y$, if a Hilbert-Schmidt norm of $\Sigma_{XY}$ is zero, X and Y are considered independent; since calculation is difficult for a kernel method, the RFFs are capable of providing a function space $\mathcal{H}_{RFF}$ to achieve the objective, and a cross-covariance matrix $\Sigma_{XY}$ is expressed as:

$$\Sigma_{XY} = \frac{1}{n-1}\sum_{i=1}^{n} \left[ (u(X_i) - \overline{m_u})^T \cdot (v(Y_i) - \overline{m_v}) \right] \quad (7)$$

where $$\overline{m_u} = \frac{1}{n}\sum_{i=1}^{n} u(X_i), \overline{m_v} = \frac{1}{n}\sum_{i=1}^{n} v(Y_i);$$

and u and v are elements in a random Fourier space;

theoretically detecting the independence between the two vectors $q_i, q_j$, substituting the vectors $q_i, q_j$ respectively as $X_i$ and $Y_i$ into the formulas (6) and (7), where whether the cross-covariance operator $\Sigma_{ST}$ regarding $u(q_i)$ and $v(q_j)$ tends to 0 needs to be determined, and the elements u and v in the random Fourier space are expressed as:

$$u(q_i) = \left(u_1(q_i), u_2(q_i), \ldots, u_{n_{q_i}}(q_i)\right), u_r(q_i) \in \mathcal{H}_{RFF}, \forall\, r \qquad (8)$$

$$v(q_j) = \left(v_1(q_j), v_2(q_j), \ldots, v_{n_{q_j}}(q_j)\right), v_r(q_j) \in \mathcal{H}_{RFF}, \forall\, r \qquad (9)$$

where $n_{q_i}$ and $n_{q_j}$ each represent a number of functions sampled from $\mathcal{H}_{RFF}$; and r represents an index of elements in u and v;

establishing a cross-covariance matrix, minimizing the Frobenius norm of the cross-covariance matrix to achieve an objective of uncorrelation, and defining a loss function as:

$$\mathcal{L}_{dec} = \lambda \Sigma_{1 \leq i, j \leq m_Q} \left\| \Sigma_{q_i, q_j} \right\|_F^2 \qquad (10)$$

where $m_Q$ represents a dimension of Q; F represents a norm; and hyper-parameter A represents sigmoid ramp-up, which is in the following form according to a function with a number of training epochs increasing from 0:

$$\lambda(t) = e^{-5(1-t)^2} \qquad (11)$$

where the $t \in [0, \text{epoch}]$;

step 4-2, fully mining the identity information output by the primary brainprint disentangling neural network using an adversarial self-supervised network, specifically including:

step 4-2-1, inputting the identity feature S output by the EEG feature extraction network $G_f$ to the adversarial self-supervised network H to obtain a mask representation; taking each dimension of the mask representation as a discrete random variable, and sampling each dimension to obtain an approximate K–hotvector, and defining β representing approximate sampling of a κ–hot vector by Gumbel-Softmax trick as:

$$\beta = Gumbel - Softmax(H(S), \kappa N) \in \mathbb{R}^N \qquad (12)$$

where $\kappa \in (0,1)$; N represents dimensions obtained by the adversarial self-supervised network; a mask closest to 1 in κN after sampling from a result is taken as an important feature, and other mask is taken as a secondary feature; and defining Gumbel-Softmax: for pre-defined $\tau > 0, i \in \{1, \ldots, N\}$, $p \in \{1, \ldots, \kappa\}$, deriving:

$$\beta_i = \max_{p \in 1, \ldots \kappa} \frac{\exp\left((\log \pi_i + \varepsilon_i^p)/\tau\right)}{\sum_{j=1}^N \exp\left((\log \pi_i + \varepsilon_i^p)/\tau\right)} \qquad (13)$$

where $\pi = H(S) \in \mathbb{R}^N$ represents a probability vector $$\varepsilon_1^p \ldots \varepsilon_K^p$$

represent samples complying with a Gumbel distribution; and $\pi_i \geq 0$, $i \in 1, \ldots, N$, $\Sigma_i \pi_i = 1$; and step 4-2-2, multiplying the identity feature S output by the EEG feature extraction network $G_f$ by masks β and 1–β to obtain an important dimension feature and a secondary dimension feature, and utilizing the main classifier C and the auxiliary classifier $C_S$ to train the adversarial self-supervised network H to fully utilize a discriminable identity feature;

redefining $\mathcal{L}^s$ of the formula (2)

as a loss function of the main classifier C:

$$\mathcal{L}_s^{sup} = \ell(C(S \circ \beta), S) \qquad (14)$$

wherein l represents a cross entropy loss; and as a loss function of the auxiliary classifier $C_S$:

$$\mathcal{L}_s^{inf} = \mathcal{L}(C_S(S \circ (1 - \beta)), S) \qquad (15)$$

where ○ represents point multiplication;

firstly minimizing the loss functions to train and optimize the EEG feature extraction networks $G_f$, $G_t$, the main classifier C, and the auxiliary classifier $C_S$; and secondly minimizing $$\mathcal{L}_s^{sup}$$

and maximizing $$\mathcal{L}_s^{inf}$$

to train the adversarial self-supervised network H:

$$\min_{G_t, G_f, G_A, C, C_S} \mathcal{L}_s^{sup} + \mathcal{L}_s^{inf} + \mathcal{L}_t + \lambda \mathcal{L}_{dec} \qquad (16)$$

$$\min_H \mathcal{L}_s^{sup} - \mathcal{L}_s^{inf} \qquad (17)$$

wherein $\mathcal{L}_t$ represents a cross entropy loss of the task classifier; step 5, verifying and testing the trained primary brainprint and task disentangling neural network model; and step 6, performing brainprint recognition on an EEG using the trained, verified, and tested primary brainprint and task disentangling neural network model.

Preferably, step 1 may specifically include:

step 1-1, downsampling EEG data to 250 Hz, and filtering the original EEG data at 0 to 75 Hz using a Butterworth filter;

step 1-2, performing short-time Fourier transform on the EEG data x processed in step 1-1 to extract time-frequency features;

step 1-3, intercepting the time-frequency features obtained in step 1-2 using a time window, adding to each time-frequency feature a tag of a subject to which the time-frequency feature belongs and a corresponding task tag; and step 1-4, using one task of EEG sample data obtained in step 1-3 as a test set $\{X_t, Y_t, Y_{tl}\}$, and proportionally dividing remaining samples into a training set $$\{X_{sj}, Y_{sj}, Y_{slj}\}_{j=1}^{K}$$

and a validation set $\{X_v, Y_v, Y_{vi}\}$, where X, Y, $Y_l$, and K represent a sample, an identity tag, a task tag, and a number of tasks, respectively.

Preferably, step 1-2 may specifically include:

using a time-limited window function h(t), assuming that a non-stationary signal x is stationary within one time window, performing piecewise analysis on the signal x by moving of the window function h(t) on a time axis to obtain a set of local "frequency spectra" of the signal, and defining the short-time Fourier transform of signal x(τ) as:

$$STFT(t, f) = \int_{-\infty}^{\infty} x(\tau)h(\tau - t)e^{-j2\pi f\tau}d\tau \tag{1}$$

where STFT(t,f) represents the short-time Fourier transform of the signal x(τ) in time t and frequency f, and h(τ−t) represents the window function.

Preferably, in step 2-1, the low frequency may be 1 to 12 Hz, and the high frequency may be 12 to 30 Hz.

Preferably, in step 2-3, the kernel sizes of the two layers of one-dimensional time-domain convolutions may be [(6× 1), (7×1)], [(7×1), (11×1)], and [(15×1), (15×1)], respectively, and the kernel sizes of the one layer of one-dimensional frequency-domain convolution may be (12×1), (18× 1), and (30×1), respectively.

Preferably, the loss functions (16) and (17) may be optimized by gradient back propagation.

In a second aspect, the present disclosure provides a task-independent brainprint recognition apparatus, including:

a data acquisition module configured to acquire EEG data;

a data preprocessing module configured to preprocess the EEG data; and a brainprint recognition module configured to use a trained, verified, and tested primary brainprint and task disentangling neural network model.

In a third aspect, the present disclosure provides a computer-readable storage medium, storing a computer program, where the computer program, when executed in a computer, causes the computer to perform the task-independent brainprint recognition method based on feature disentanglement by decorrelation described above.

In a fourth aspect, the present disclosure provides a computing device, including a memory and a processor, where an executable code is stored in the memory, and the processor, when executing the executable code, performs the task-independent brainprint recognition method based on feature disentanglement by decorrelation described above.

The present disclosure has the following beneficial effects: for EEG data under different task stimuli, the present disclosure firstly allows for coarse-grained decomposition of identity information and task related information in the electroencephalogram. Further, in consideration of the nonstationarity of the EEG, a brainprint feature and a task feature are disentangled by decorrelation. Finally, by adversarial self-supervision, all identity related features are fully utilized as much as possible, rendering a model stable across time and across tasks.

DETAILED DESCRIPTION OF THE EMBODIMENTS

To make the objective, technical solutions, and advantages of the present disclosure clearer, the present disclosure will be further described in detail with reference to the technical solutions of the present disclosure and the accompanying drawings.

Figure 1:
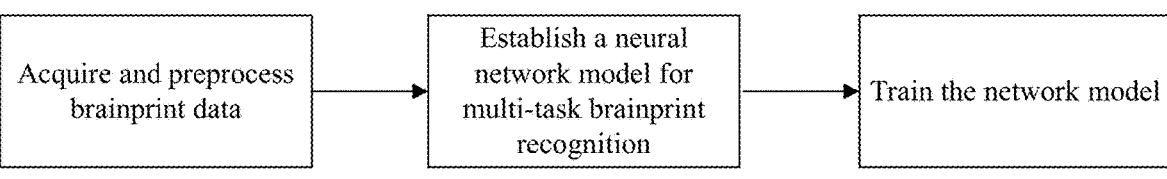
FIG. 1 is a flowchart of a brainprint recognition model provided in the present disclosure.
Figure 2:
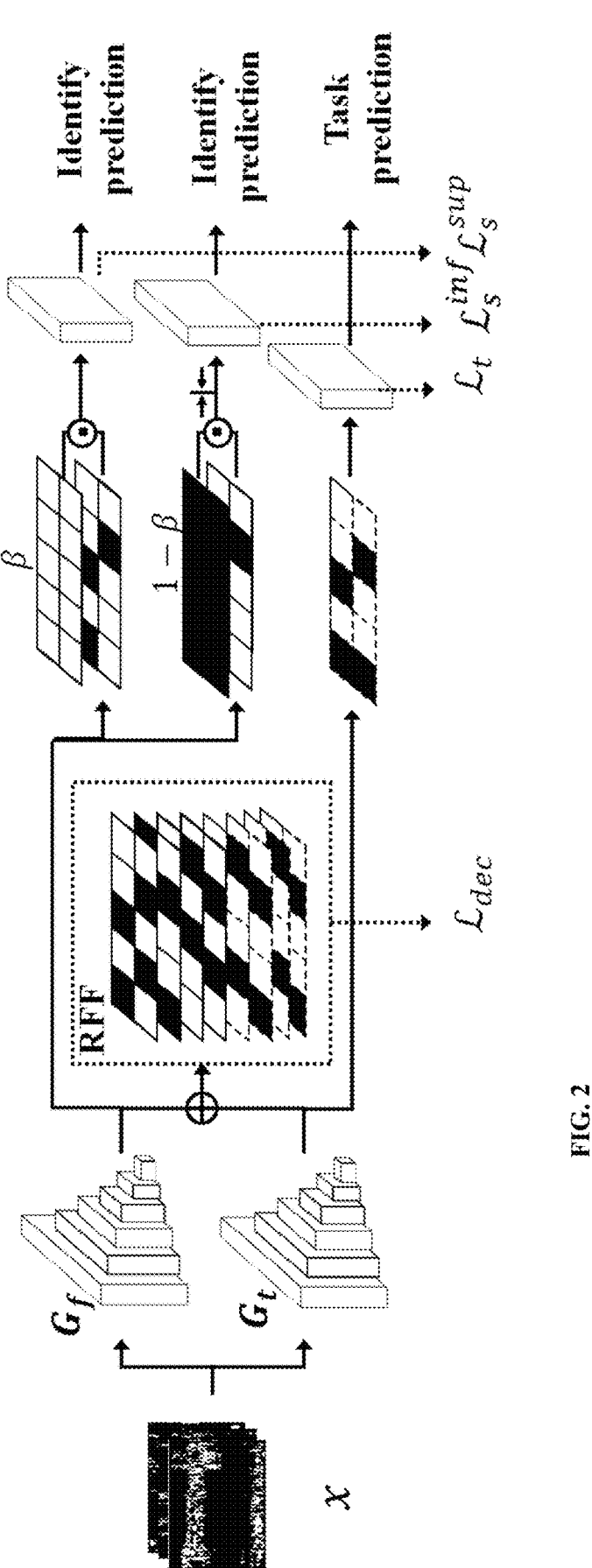
FIG. 2 is an architecture diagram of a task-independent brainprint recognition model based on feature disentanglement by decorrelation provided in the present disclosure.

The present disclosure provides a task-independent brainprint recognition method based on feature disentanglement by decorrelation, and a flowchart thereof is as shown in FIG. 1. Firstly, an original EEG is preprocessed based on fast Fourier transform. Secondly, two branch networks are used to perform coarse-grained decomposition of identity information and task related information in the EEG. Subsequently, in consideration of an influence of a task state on the identity information, a decorrelating method is employed such that the identity information and the task related information are independent as much as possible. Finally, a task related brainprint feature in the EEG is fully utilized for classification by adversarial self-supervision.

Step 1, original EEG data is preprocessed.

1) An original EEG signal contains a noise frequency of typically lower than 0.5 Hz or higher than 50 Hz. To remove power frequency interference caused by an EEG acquisition device and myoelectric interference of a subject, the EEG data is downsampled to 250 Hz, and the original EEG data is filtered at 0 to 75 Hz using a Butterworth filter.

2) Short-time Fourier transform is performed on a signal x output in operation 1) to extract time-frequency features. A time-limited window function h(t) is used. Assuming that a non-stationary signal x is stationary within one time window, piecewise analysis is performed on the signal x by moving of the window function h(t) on a time axis to obtain a set of local "frequency spectra" of the signal. A specific window size of the present disclosure is 0.5 s. The short-time Fourier transform of the signal x(τ) is defined as:

$$STFT(t, f) = \int_{-\infty}^{\infty} x(\tau)h(\tau - t)e^{-j2\pi f\tau}d\tau \tag{1}$$

STFT(t,f) represents the short-time Fourier transform of the signal x(τ) in time t and frequency f, and h(τ−t) represents the window function.

3) The EEG data obtained in 2) is intercepted using a time window of 15 s, and corresponding EEG sample data is added with a tag of a subject to which the EEG sample data belongs and a corresponding task tag.

4) One task of the EEG sample data obtained in 3) is used as a test set $\{X_t,Y_t,Y_{tl}\}$, and remaining samples are proportionally divided into a training set $$\{X_{sj}, Y_{sj}, Y_{slj}\}_{j=1}^{K}$$

and a validation set $\{X_v,Y_v,Y_{vl}\}$, where X, Y, $Y_l$, and K represent a sample, an identity tag, a task tag, and a number of tasks, respectively. The EEG sample is expressed as $x \in \mathbb{R}^{c \times s \times t}$, where c represents a number of EEG channels; s represents a number of frequency-domain dimensions; and t represents a number of time-domain dimensions. Specifically, nine channels Fz, F7, F8, C3, C4, P7, P8, O1, and O2 are selected in the present disclosure; 1 to 30 Hz, and a sampling rate of 250 Hz are adopted. That is, c=9, s=30, and t=30.

Step 2, a neural network model for extracting multi-scale time-frequency brainprint features is established.

1) Each EEG sample is divided into three subsamples by three frequency bands: 1 to 12 Hz, 12 to 30 Hz, and a full frequency band, and time-domain brainprint features are extracted using one-dimensional time-domain convolution kernels of (1×21), (1×5), and (1×11), respectively.

2) Frequency-domain brainprint features of low-frequency, high-frequency, and full-frequency EEGs are extracted using two layers of one-dimensional frequency-domain convolution kernels of [(6×1), (7×1)], [(7×1), (11× 1)], and [(15×1), (15× 1)], respectively.

3) By the extraction of the time-domain and frequency-domain features, $$\{f_i \in \mathbb{R}^{n \times c}\}_{i=1}^{3}$$

time-frequency feature is obtained for each sample, where n represents a number of hidden layers.

4) The time-frequency brainprint features are spliced by frequency-domain dimensions to obtain a time-frequency feature $f_{ts} \in \mathbb{R}^{n \times c \times 3}$; channel-wise and spatial convolutions are then performed on the time-frequency feature $f_{ts}$ with a two-dimensional convolution kernel of (9×3), and a time-frequency-space feature $f \in \mathbb{R}^{n}$ of the brainprint is output.

Step 3, a primary brainprint and task disentangling neural network model is established.

1) An EEG feature extraction network $G_f$ described in step 2 is established to extract identity information, and a fully connected layer is used to establish an identity discriminator $C_f$ for identity recognition, where the identity discriminator $C_f$ includes a main classifier C and an auxiliary classifier Cs:

$$\mathcal{L}_s = -\frac{1}{n}\sum_{i=1}^{m}\hat{P}\log C_f(G_f(x_i)) = -\frac{1}{n}\sum_{i=1}^{m}\hat{P}\log C_f(f), \tag{2}$$

where $\mathcal{L}_s$ represents the loss function; n represents a number of samples; m represents a number of subjects; and $\hat{P}$ represents a probability that input data $x_i$ belongs to subject m;

2) An EEG feature extraction network $G_t$ described in step 2 is established to extract task information, and a fully connected layer is used to establish a task discriminator $C_t$ for task discrimination.

Step 4, constraint conditions for the EEG feature extraction networks $G_f$ and $G_t$ during training are established: the identity information $S=G_f(x)$ and the task information $A=G_t(x)$ are decorrelated.

4) An original identity feature matrix S and an original task feature matrix A output by the EEG feature extraction networks $G_f$ and $G_t$ to obtain a new matrix. The matrix Q is then mapped to a high-dimensional reproducing kernel Hilbert space (RKHS), and a dependency relationship between any two vectors $q_i,q_j$ in the matrix Q is determined by a Hilbert-Schmidt independence criterion (HSIC). A Frobenius norm of a cross-covariance operator in the RKHS is calculated. An independent representation for a kernel function is acquired by mapping original data to the RKHS, as shown below:

$$\mathcal{K}(x;) = \Sigma_i \alpha_i \varphi_i(x)\varphi_i(\cdot) = \left(\sqrt{\alpha_i}\,\varphi_i(x), \cdots\right)_{\mathcal{H}} \tag{3}$$

where $\mathcal{K}(\bullet,\bullet)$ represents a measurable symmetric positive definite kernel function; $\varphi$ represents a mapping function; $(\bullet)$ $\mathcal{H}$ represents a Hilbert space; and $\alpha_i$ represents a feature value. The function $\varphi$ maps the original data to a high-dimensional space, and the kernel function is derived from an inner product of the mapping function in the high-dimensional space.

5) The independence of the vectors $q_i,q_j$ is detected by the HSIC after acquiring the kernel function. For random variables $q_i,q_j$ and kernel functions $\mathcal{K}1$, $\mathcal{K}2$, the HSIC is defined as:

$$HSIC^{\mathcal{K}1,\mathcal{K}2}(q_i, q_j) := \left\|C_{q_i,q_j}^{\mathcal{K}1,\mathcal{K}2}\right\|_F^2 \tag{4}$$

where $C^{\mathcal{K}1,\mathcal{K}2}$ represents the cross-covariance operator regarding the kernel functions $\mathcal{K}1$ and $\mathcal{K}2$ in the RKHS; and $\|\bullet\|_F$ is the Frobenius norm. Moreover, there exists $HSIC^{\mathcal{K}1,\mathcal{K}2}(q_i,q_j)=0 \Leftrightarrow q_i \perp q_j$, with $q_i$ being independent of $q_j$.

6) The kernel function $\mathcal{K}(x,\bullet)$ is optimized.

The present disclosure proposes approximating the kernel function using random Fourier features (RFF) due to a high complexity of calculating the kernel function $\mathcal{K}(x,\bullet)$ in the Hilbert space. A dimension-reduced function is acquired by Fourier transform sampling to approximate the original kernel function, and a nonlinear correlation of the two vectors $q_i,q_j$ is captured. Specific steps are as follows:

The vectors $q_i,q_j$ are mapped to a low-dimensional Euclidean space using the RFFs by the following formula (5), and an inner product after the mapping is an estimated value of the kernel function. Linear calculation is performed using the RFFs to remove the nonlinear correlation to realize statistical independence of the features.

A random Fourier function space $\mathcal{H}_{RFF}$ is expressed as:

$$\mathcal{H}_{RFF} = \{h:x \to \sqrt{2}\,\cos(\omega x + \phi) \mid \omega \sim N(0, 1), \phi[U(0, 2\pi)]; \tag{5}$$

where $\omega$ represents sampling from a standard normal distribution; and $\varphi$ represents sampling from a uniform distribution.

The matrix Q is transformed into the RFFs by the formula (5) to approximate the kernel functions $\mathcal{K}(x,\cdot)$ of an identity feature and a task feature.

4) The independence is detected.

It is assuming that there exist measurable spaces $\Omega_1$ and $\Omega_2$, where ($\mathcal{H}1, \mathcal{K}1$) and ($\mathcal{H}2, \mathcal{K}2$) represent the RKHSs in $\Omega_1$ and $\Omega_2$, and correspondingly, $\mathcal{K}1$ and $\mathcal{K}2$ are also measurable. There exists a unique cross-covariance operator $\Sigma_{XY}$ in a space from $\mathcal{H}_1$ to $\mathcal{H}_2$, deriving:

$$\langle g, \Sigma_{XY} f \rangle = Cov(f(X), g(Y)) = \mathbb{E}_{XY}[f(X)g(Y)] - \mathbb{E}_X[f(x)]\mathbb{E}_Y[g(Y)] \quad (6)$$

where $f(X) \in \mathcal{H}_1$, $g(Y) \in \mathcal{H}_2$, and $Cov(\cdot)$ represents a covariance matrix.

As shown in the Formula (6), the calculation of $\Sigma_{XY}$ is expanded to the calculation of the covariance matrix over the Euclidean space, and $f(X)$ and $g(Y)$ represent nonlinear kernel functions. Due to $\Sigma_{XY}=0 \Leftrightarrow X \perp Y$, if a Hilbert-Schmidt norm of $\Sigma_{XY}$ is zero, X and Y are considered independent. Since calculation is difficult for a kernel method, the RFFs are capable of providing a function space $\mathcal{H}_{RFF}$ to achieve the objective, and a cross-covariance matrix $\Sigma_{XY}$ may be expressed as:

$$\sum_{XY} = \frac{1}{n-1}\sum_{i=1}^{n}\left[(u(X_i) - \overline{m_u})^T \cdot (v(Y_i) - \overline{m_v})\right]; \quad (7)$$

$$\text{where } \overline{m_u} = \frac{1}{n}\sum_{i=1}^{n}u(X_i), \overline{m_v} = \frac{1}{n}\sum_{i=1}^{n}v(Y_i).$$

Theoretically, the independence between the two vectors $q_i, q_j$ (replaced by X, Y as described above) is detected. Whether the cross-covariance operator $\Sigma_{ST}$ regarding $u(q_i)$ and $v(q_j)$ tends to 0 needs to be determined, and u and v are elements in the random Fourier space, expressed as:

$$u(q_i) = \left(u_1(q_i), u_2(q_i), \ldots, u_{n_{q_i}}(q_i)\right), u_r(q_i) \in \mathcal{H}_{RFF}, \forall r \quad (8)$$

$$v(q_j) = \left(v_1(q_j), v_2(q_j), \ldots, v_{n_{q_j}}(q_j)\right), v_r(q_j) \in \mathcal{H}_{RFF}, \forall r \quad (9)$$

where ng; and ng; each represent a number of functions sampled from $\mathcal{H}_{RFF}$.

A cross-covariance matrix is established; the Frobenius norm of the cross-covariance matrix is minimized to achieve an objective of uncorrelation, and a loss function is defined as:

$$\mathcal{L}_{dec} = \lambda \Sigma_{1 \leq i,j \leq m_Q}\left\|\Sigma_{q_i,q_j}\right\|_F^2 \quad (10)$$

where hyper-parameter $\lambda$ represents sigmoid ramp-up, which is in the following form according to a function with a number of training epochs increasing from 0:

$$\lambda(t) = e^{-5(1-t)^2}. \quad (11)$$

Step 5, an adversarial self-supervised module is established to fully utilize the identity information.

1) The identity feature S output by $G_f$ is input to the adversarial self-supervised network H to obtain a mask representation. Each dimension of the mask representation is taken as a discrete random variable, and each dimension is sampled to obtain an approximate K−hotvector. $\beta$ representing approximate sampling of a vector by Gumbel-Softmax-trick κ−hot is defined as:

$$\beta = Gumbel - Softmax(H(S), \kappa N) \in \mathbb{R}^N \quad (12)$$

where $\kappa \in (0,1)$; N represents dimensions obtained by the adversarial self-supervised network; a mask closest to 1 in κN after sampling from a result is taken as an important feature, and other mask is taken as a secondary feature.

Gumbel-Softmax is defined: for pre-defined $\tau>0$, $i \in \{1, \ldots, N\}$, $p \in \{1, \ldots, \kappa\}$, the following formula is derived:

$$\beta_i = \max_{p=1,\ldots,\kappa}\frac{\exp\left((\log\pi_i + \varepsilon_i^p)/\tau\right)}{\sum_{j=1}^{N}\exp\left((\log\pi_j + \varepsilon_j^p)/\tau\right)}, \quad (13)$$

where $\pi=H(S) \in \mathbb{R}^N$ represents a probability vector; represent samples $$\varepsilon_1^p \ldots \varepsilon_K^p$$

represent samples complying with a Gumbel distribution; and $\pi_i \geq 0$, $i \in 1, \ldots, N$, $\Sigma_i\pi_i=1$. It is set that $\tau=0.8$.

2) The identity feature S output by $G_f$ is multiplied by masks $\beta$ and $1-\beta$ to obtain an important dimension feature and a secondary dimension feature, and the main classifier C and the auxiliary classifier $C_S$ are utilized. $\mathcal{L}_s$ of the formula (2) may be redefined as:

a loss function of the main classifier $$\mathcal{L}_s^{sup} = \ell(C(S \circ \beta), s); \quad (14)$$

and a loss function of the auxiliary classifier $$\mathcal{L}_s^{inf} = \ell(C_S(S \circ (1 - \beta)), s). \quad (15)$$

Firstly, the loss functions are minimized to train and optimize the EEG feature extraction networks $G_f$, $G_r$, the main classifier C, and the auxiliary classifier $C_S$. Secondly, $$\mathcal{L}_s^{sup}$$

is minimized and $$\mathcal{L}_s^{inf}$$

13 is maximized to train the adversarial self-supervised network H:

$$\min_{G_t,G_f,G_A,C,C_S} \mathcal{L}_s^{sup} + \mathcal{L}_s^{inf} + \mathcal{L}_t + \lambda\mathcal{L}_{dec}; \tag{16}$$

$$\min_{H} \mathcal{L}_s^{sup} - \mathcal{L}_s^{inf}. \tag{17}$$

The proposed adversarial self-supervised module may allow secondary dimensions to play a role. The optimized auxiliary classifier $C_S$ uses the secondary dimensions to classify tags to minimize the loss function $$\mathcal{L}_s^{inf},$$

and the self-supervised network learns β to select a favorable dimension to maximize the loss function $$\mathcal{L}_s^{inf}.$$

Therefore, a secondary dimension having a low contribution can be found. The classifier is adversarial to a mask network. By optimizing $G_f$ and $G_t$ to minimize $$\mathcal{L}_s^{inf}$$

and $\mathcal{L}_{dec}$, a disadvantageous dimension is forced to carry more identity features that are independent of the task features. Finally, low-level representations are removed repeatedly and turned into new advanced representations, and learned representations more tend to clean identity features.

Step 6, the network model is trained.

The training set obtained in step 1.4 is used to optimize the loss functions by gradient back propagation for the model established in step 2 to step 5, and the best model is saved by using the validation set obtained in step 1.4 for testing.

A stochastic gradient descent (SGD) optimizer is used; a learning rate is 0.025; and batch_size is 64.

Step 7, the effectiveness of the present disclosure is verified on the multi-task identity recognition data set, including 30 subjects (N=30). A contrast experiment is conducted with existing methods, and results are as shown in Table 1. The verification results indicate that the model proposed in the present disclosure is capable of effectively brainprint features under different cognitive tasks, is not limited to the cognitive tasks, and has good robustness.

TABLE 1

Accuracy Rate and Equal Error Rate of Model
on Multi-Task Identity Recognition Data Set

| Model | ACC | EER |
|---|---|---|
| UBM-GMM | 71.2 | 10.9 |
| i-vector | 70.5 | 10.6 |
| x-vector | 67.1 | 11.3 |
| EEGNet | 70.1 | 9.2 |
| EEGNet(PSD) | 77.5 | 5.79 |

14

TABLE 1-continued

Accuracy Rate and Equal Error Rate of Model
on Multi-Task Identity Recognition Data Set

| Model | ACC | EER |
|---|---|---|
| CNN-RNN | 77.8 | 6.24 |
| modified-i-vector | 85.1 | 5.81 |
| modified-x-vector | 76.8 | 8.16 |
| ix-vector | 86.4 | 5.02 |
| Present disclosure | 90.2 | 3.17 |

What is claimed is:

1. A task-independent brainprint recognition method based on feature disentanglement by decorrelation, comprising the following steps:

step 1, preprocessing original electroencephalogram (EEG) data and establishing a data set;

step 2, establishing an EEG feature extraction network for extracting a multi-scale time-frequency-space feature of a brainprint, specifically comprising:

step 2-1, dividing each EEG sample into low-frequency, high-frequency, and full-frequency subsamples by a low frequency band, a high frequency band, and a full frequency band;

step 2-2, separately subjecting low-frequency, high-frequency, and full-frequency time-frequency features to two layers of one-dimensional time-domain convolutions and one layer of one-dimensional frequency-domain convolution having different kernel sizes to extract advanced time-frequency brainprint features of low-frequency, high-frequency, and full-frequency EEGs;

step 2-3, obtaining a time-frequency brainprint feature $$\{f_i \in \mathbb{R}^{n \times c}\}_{i=1}^3$$

of each EEG sample by extracting a time-domain brainprint feature and a frequency-domain brainprint feature, wherein $\mathbb{R}$ represents a set of real numbers, n represents a number of hidden layers, and c represents a number of EEG channels; and step 2-4, splicing the time-frequency brainprint features by frequency-domain dimensions to obtain a time-frequency feature $f_{ts} \in \mathbb{R}^{n \times c \times 3}$, then performing channel-wise and spatial convolutions on the time-frequency feature $f_{ts}$ with a two-dimensional convolution kernel of (c×3), and outputting the multi-scale time-frequency-space feature $f \in \mathbb{R}^n$ of the brainprint;

step 3, establishing a primary brainprint and task disentangling neural network model;

wherein the primary brainprint and task disentangling neural network model comprises a primary brainprint disentangling neural network and a primary task disentangling neural network that are concurrent;

the primary brainprint disentangling neural network comprises an EEG feature extraction network $G_t$ and an identity discriminator $C_t$; the EEG feature extraction network $G_f$ is configured to extract identity information, and is the EEG feature extraction network established in step 2; the identity discriminator $C_f$ is configured for identity recognition, and comprises a main classifier C and an auxiliary classifier Cs that are concurrent; and the main classifier C and the auxiliary classifier Cs are both fully connected layers;

a loss function of the EEG feature extraction network $G_f$ is as follows:

$$\mathcal{L}_s = -\frac{1}{n}\sum_{i=1}^{m}\hat{P}\log C_f(G_f(x_i)) = -\frac{1}{n}\sum_{i=1}^{m}\hat{P}\log C_f(f) \tag{2}$$

wherein $\mathcal{L}_s$ represents the loss function; n represents a number of samples; m represents a number of subjects; and $\hat{P}$ represents a probability that input data $x_i$ belongs to subject m;

the primary task disentangling neural network comprises an EEG feature extraction network $G_t$ and a task classifier $C_t$; the EEG feature extraction network $G_t$ is configured to extract task information, and is the EEG feature extraction network established in step 2; and the task classifier $C_t$ is configured for task discrimination, and is a fully connected layer;

step 4, training the primary brainprint and task disentangling neural network model training, specifically comprising:

step 4-1, establishing constraint conditions for the EEG feature extraction networks $G_f$ and $G_t$: decorrelating the identity information $S=G_f(x)$ and the task information $A=G_t(x)$, specifically comprising:

1) splicing an original identity feature matrix S and an original task feature matrix A output by the EEG feature extraction networks $G_f$ and $G_t$ to obtain a new matrix $Q \in \mathbb{R}^{m_S \times m_Q}$, wherein $m_S$ represents a number of samples, and $m_Q$ represents feature dimensions; mapping the matrix Q to a high-dimensional reproducing kernel Hilbert space (RKHS), and determining a dependency relationship between any two vectors $q_i$, $q_j$ in the matrix Q by a Hilbert-Schmidt independence criterion (HSIC), wherein $i,j \in m_Q$; and calculating a Frobenius norm of a cross-covariance operator in the RKHS;

acquiring an independent representation for a kernel function by mapping original data to the RKHS, as shown below:

$$\mathcal{K}(x,\cdot) = \sum_{i}\alpha_i\varphi_i(x)\varphi_i(\cdot) = \left(\sqrt{\alpha_i}\,\varphi_i(x), \cdots\right)_{\mathcal{H}} \tag{3}$$

wherein $\mathcal{K}(\cdot,\cdot)$ represents a measurable symmetric positive definite kernel function; $\varphi$ represents a mapping function; $(\cdot)$ $\mathcal{H}$ represents a Hilbert space; and $\alpha_i$ represents a feature value;

2) detecting independence of the vectors $q_i$, $q_j$ by the HSIC after acquiring the kernel function;

for random variables $q_i$, $q_j$ and kernel functions $\mathcal{K}1$, $\mathcal{K}2$, defining the HSIC as:

$$HSIC^{\mathcal{K}1,\mathcal{K}2}(q_i, q_j) := \left\|C_{q_i,q_j}^{\mathcal{K}1,\mathcal{K}2}\right\|_F^2 \tag{4}$$

wherein $C^{\mathcal{K}1,\mathcal{K}2}$ represents the cross-covariance operator regarding the kernel functions $\mathcal{K}1$ and $\mathcal{K}2$ in the RKHS; $\|\cdot\|_F$ is the Frobenius norm; and there exists $HSIC^{\mathcal{K}1,\mathcal{K}2}(q_i,q_j)=0 \Leftrightarrow q_i \perp q_j$, with $q_i$ being independent of $q_j$;

3) optimizing the kernel function $\mathcal{K}(x,\cdot)$;

approximating the kernel function using random Fourier features (RFF) due to a high complexity of calculating

16 the kernel function $\mathcal{K}(x,\cdot)$ in the Hilbert space, acquiring a dimension-reduced function by Fourier transform sampling to approximate an original kernel function, and capturing a nonlinear correlation of the two vectors $q_i,q_j$, specifically comprising:

mapping the vectors $q_i,q_j$ to a low-dimensional Euclidean space using the RFFs by the following formula (5), and obtaining an inner product after the mapping as an estimated value of the kernel function; performing linear calculation using the RFFs to remove the nonlinear correlation to realize statistical independence of the vectors $q_i,q_j$;

expressing a random Fourier function space $\mathcal{H}_{RFF}$ as:

$$\mathcal{H}_{RFF} = \left\{ h: x \to \sqrt{2}\,\cos(\omega x + \phi)\,\big|\,\omega \sim N(0,1), \phi \sim U(0,2\pi)\right\} \tag{5}$$

wherein h represents a random Fourier feature mapping function; $\omega$ represents sampling from a standard normal distribution $N(0,1)$; $\phi$ represents sampling from a uniform distribution $U(0,2\pi)$; and x represents the vectors $q_i,q_j$; and transforming the matrix Q into the RFFs by the formula (5) to approximate the kernel functions $\mathcal{K}(x,\cdot)$ of the identity feature and a task feature;

4) detecting the independence of the vectors $q_i,q_j$;

assuming that there exist measurable spaces $\Omega_1$ and $\Omega_2$, wherein $(\mathcal{K}_1, \mathcal{H}_1)$ and $(\mathcal{H}_2, \mathcal{K}_2)$ represent the RKHSs in $\Omega_1$ and $\Omega_2$, and correspondingly, $\mathcal{K}_1$ and $\mathcal{K}_2$ are also measurable, and a unique cross-covariance operator $\Sigma_{XY}$ exists in a space from $\mathcal{H}_1$ to $\mathcal{H}_2$, deriving:

$$\left\langle g, \sum_{XY} f\right\rangle = Cov(f(X), g(Y))\right) = \mathbb{E}_{XY}[f(X)g(Y)] - \mathbb{E}_X[f(X)]\mathbb{E}_Y[g(Y)] \tag{6}$$

wherein $f(X) \in \mathcal{H}_1$, $g(Y) \in \mathcal{H}_2$, and $Cov(\cdot)$ represents a covariance matrix; and $\mathbb{E}_{xy}$, $\mathbb{E}_x$, and $\mathbb{E}_y$ represent mathematical expectations, as shown in the Formula (6), the calculation of $\Sigma_{XY}$ is expanded to a calculation of the covariance matrix over the Euclidean space, and $f(X)$ and $g(Y)$ represent nonlinear kernel functions; due to $\Sigma_{XY}=0 \Leftrightarrow X \perp Y$, if a Hilbert-Schmidt norm of $\Sigma_{XY}$ is zero, X and Y are considered independent; since calculation is difficult for a kernel method, the RFFs are capable of providing a function space $\mathcal{H}_{RFF}$ to achieve an objective, and a cross-covariance matrix $\Sigma_{XY}$ is expressed as:

$$\sum_{XY} = \frac{1}{n-1}\sum_{i=1}^{n}\left[(u(X_i) - \overline{m_u})^T \cdot (v(Y_i) - \overline{m_v})\right] \tag{7}$$

wherein $$\overline{m_u} = \frac{1}{n}\sum_{i=1}^{n}u(X_i), \overline{m_v} = \frac{1}{n}\sum_{i=1}^{n}v(Y_i);$$

u and v are elements in a random Fourier space; and T represents a transpose operation;

theoretically detecting the independence between the two vectors $q_i,q_j$, substituting the vectors $q_i,q_j$ respectively as $X_i$ and $Y_i$ into the formulas (6) and (7), wherein whether a cross-covariance operator $\Sigma_{ST}$ regarding $u(q_i)$ and $v(q_j)$ tends to 0 needs to be determined, and the elements u and v in the random Fourier space are expressed as:

$$u(q_i) = \left(u_1(q_i), u_2(q_i), \ldots, u_{n_{q_i}}(q_i)\right), u_r(q_i) \in \mathcal{H}_{RFF}, \forall r \quad (8)$$

$$v(q_j) = \left(v_1(q_j), v_2(q_j), \ldots, v_{n_{q_j}}(q_j)\right), v_r(q_j) \in \mathcal{H}_{RFF}, \forall r \quad (9)$$

wherein $n_{q_i}$ and $n_{q_j}$ each represent a number of functions sampled from $\mathcal{H}_{RFF}$; and r represents an index of elements in u and v;

establishing a second cross-covariance matrix, minimizing the Frobenius norm of the second cross-covariance matrix to achieve an objective of uncorrelation, and defining a loss function as:

$$\mathcal{L}_{dec} = \lambda \sum_{1 \le i, j \le m_Q} \left\| \sum_{q_i, q_j} \right\|_F^2 \quad (10)$$

wherein $m_Q$ represents a dimension of Q; F represents a norm; and hyper-parameter $\lambda$ represents sigmoid ramp-up, which is in the following form according to a function with a number of training epochs increasing from 0:

$$\lambda(t) = e^{-5(1-t)^2} \quad (11)$$

wherein $t \in [0, \text{epoch}]$; and step 4-2, fully mining the identity information output by the primary brainprint disentangling neural network using an adversarial self-supervised network, specifically comprising:

step 4-2-1, inputting the identity feature S output by the EEG feature extraction network $G_f$ to the adversarial self-supervised network H to obtain a mask representation; taking each dimension of the mask representation as a discrete random variable, and sampling each dimension to obtain an approximate K–hotvector, and defining $\beta$ representing approximate sampling of a $\kappa$–hotvector by Gumbel-Softmax trick as:

$$\beta = Gumbel - Softmax(H(S), \kappa N) \in \mathbb{R}^N \quad (12)$$

wherein $\kappa \in (0,1)$; N represents dimensions obtained by the adversarial self-supervised network; a mask closest to 1 in $\kappa N$ after sampling from a result is taken as an important feature, and other mask is taken as a secondary feature; and defining Gumbel-Softmax: for pre-defined $\tau > 0$, $i \in \{1, \ldots, N\}$, $p \in \{1, \ldots, \kappa\}$, deriving:

$$\beta_i = \max_{p \in 1, \ldots, \kappa} \frac{\exp\left((\log \pi_i + \varepsilon_i^p)/\tau\right)}{\sum_{j=1}^N \exp\left((\log \pi_j + \varepsilon_j^p)/\tau\right)} \quad (13)$$

wherein $\pi = H(S) \in \mathbb{R}^N$ represents a probability vector;

$$\varepsilon_1^p \ldots \varepsilon_K^p$$

represent samples complying with a Gumbel distribution; and $\pi_i \ge 0$, $i \in 1, \ldots, N$, $\Sigma_i \pi_i = 1$; and step 4-2-2, multiplying the identity feature S output by the EEG feature extraction network $G_f$ by masks $\beta$ and $1-\beta$ to obtain an important dimension feature and a secondary dimension feature, and utilizing the main classifier C and the auxiliary classifier $C_S$ to train the adversarial self-supervised network H to fully utilize a discriminable identity feature;

redefining $\mathcal{L}_s$ of the formula (2) as a loss function of the main classifier C:

$$\mathcal{L}_s^{sup} = \ell(C(S \circ \beta), S) \quad (14)$$

wherein l represents a cross entropy loss;
and as a loss function of the auxiliary classifier $C_S$:

$$\mathcal{L}_s^{inf} = \ell(C_S(S \circ (1-\beta)), S) \quad (15)$$

wherein $\circ$ represents point multiplication;

firstly minimizing the loss functions to train and optimize the EEG feature extraction networks $G_f$, $G_t$, the main classifier C, and the auxiliary classifier $C_S$; and secondly minimizing $$\mathcal{L}_s^{sup}$$

and maximizing $$\mathcal{L}_s^{inf}$$

to train the adversarial self-supervised network H:

$$\min_{G_t, G_f, G_A, C, C_S} \mathcal{L}_s^{sup} + \mathcal{L}_s^{inf} + \mathcal{L}_t + \lambda \mathcal{L}_{dec} \quad (16)$$

wherein $\mathcal{L}_{dec}$ represents the loss function defined in formula (10);

$$\min_H \mathcal{L}_s^{sup} - \mathcal{L}_s^{inf} \quad (17)$$

wherein $\mathcal{L}_t$ represents a cross entropy loss of the task classifier;

step 5, verifying and testing the trained primary brainprint and task disentangling neural network model; and step 6, performing brainprint recognition on an EEG using the trained, verified, and tested primary brainprint and task disentangling neural network model.

2. The task-independent brainprint recognition method based on feature disentanglement by decorrelation according to claim 1, wherein step 1 specifically comprises:

step 1-1, downsampling EEG data to 250 Hz, and filtering the original EEG data at 0 to 75 Hz using a Butterworth filter;

step 1-2, performing short-time Fourier transform on the EEG data x processed in step 1-1 to extract time-frequency features;

step 1-3, intercepting the time-frequency features obtained in step 1-2 using a time window, adding to each time-frequency feature a tag of a subject to which the time-frequency feature belongs and a corresponding task tag; and step 1-4, using one task of EEG sample data obtained in step 1-3 as a test set $\{X_t, Y_t, Y_{tt}\}$, and proportionally dividing remaining samples into a training set $$\{X_{sj}, Y_{sj}, Y_{slj}\}_{j=1}^{K}$$

and a validation set $\{X_v, Y_v, Y_{vi}\}$, wherein X, Y, $Y_l$, and K represent a sample, an identity tag, a task tag, and a number of tasks, respectively.

3. The task-independent brainprint recognition method based on feature disentanglement by decorrelation according to claim 2, wherein step 1-2 specifically comprises:

using a time-limited window function h(t), assuming that a non-stationary signal x is stationary within one time window, performing piecewise analysis on the signal x by moving of the window function h(t) on a time axis to obtain a set of local "frequency spectra" of the signal, and defining a short-time Fourier transform of signal x(τ) as:

$$STFT(t, f) = \int_{-\infty}^{\infty} x(\tau)h(\tau - t)e^{-j2\pi f\tau}d\tau \qquad (1)$$

wherein STFT(t,f) represents the short-time Fourier transform of the signal x(τ) in time t and frequency f, and h(τ−t) represents the window function.

4. The task-independent brainprint recognition method based on feature disentanglement by decorrelation according to claim 1, wherein in step 2-1, the low frequency band is 1 to 12 Hz, and the high frequency band is 12 to 30 Hz.

5. The task-independent brainprint recognition method based on feature disentanglement by decorrelation according to claim 1, wherein in step 2-3, the kernel sizes of the two layers of one-dimensional frequency-domain convolutions are [(6×1), (7×1)], [(7×1), (11×1)], and [(15×1), (15×1)], respectively.

6. The task-independent brainprint recognition method based on feature disentanglement by decorrelation according to claim 5, wherein in step 2-3, the kernel sizes of the one layer of one-dimensional frequency-domain convolution are (12×1), (18×1), and (30×1), respectively.

7. The task-independent brainprint recognition method based on feature disentanglement by decorrelation according to claim 1, wherein in step 2-3, the kernel sizes of the one layer of one-dimensional frequency-domain convolution are (12×1), (18×1), and (30×1), respectively.

8. The task-independent brainprint recognition method based on feature disentanglement by decorrelation according to claim 1, wherein the loss functions (16) and (17) are optimized by gradient back propagation.

9. A task-independent brainprint recognition apparatus that implements the task-independent brainprint recognition method based on feature disentanglement by decorrelation according to claim 1, comprising:

a data acquisition module configured to acquire EEG data;

a data preprocessing module configured to preprocess the EEG data; and a brainprint recognition module configured to use a trained, verified, and tested primary brainprint and task disentangling neural network model.

10. The task-independent brainprint recognition apparatus according to claim 9, wherein step 1 specifically comprises:

step 1-1, downsampling EEG data to 250 Hz, and filtering the original EEG data at 0 to 75 Hz using a Butterworth filter;

step 1-2, performing short-time Fourier transform on the EEG data x processed in step 1-1 to extract time-frequency features;

step 1-3, intercepting the time-frequency features obtained in step 1-2 using a time window, adding to each time-frequency feature a tag of a subject to which the time-frequency feature belongs and a corresponding task tag; and step 1-4, using one task of EEG sample data obtained in step 1-3 as a test set $\{X_t, Y_t, Y_{tt}\}$, and proportionally dividing remaining samples into a training set $$\{X_{sj}, Y_{sj}, Y_{slj}\}_{j=1}^{K}$$

and a validation set $\{X_v, Y_v, Y_{vl}\}$, wherein X, Y, $Y_l$, and K represent a sample, an identity tag, a task tag, and a number of tasks, respectively.

11. The task-independent brainprint recognition apparatus according to claim 10, wherein step 1-2 specifically comprises:

using a time-limited window function h(t), assuming that a non-stationary signal x is stationary within one time window, performing piecewise analysis on the signal x by moving of the window function h(t) on a time axis to obtain a set of local "frequency spectra" of the signal, and defining a short-time Fourier transform of signal x(τ) as:

$$STFT(t, f) = \int_{-\infty}^{\infty} x(\tau)h(\tau - t)e^{-j2\pi f\tau}d\tau \qquad (1)$$

wherein STFT(t,f) represents the short-time Fourier transform of the signal x(τ) in time t and frequency f, and h(τ−t) represents the window function.

12. The task-independent brainprint recognition apparatus according to claim 9, wherein in step 2-1, the low frequency band is 1 to 12 Hz, and the high frequency band is 12 to 30 Hz.

13. The task-independent brainprint recognition apparatus according to claim 9, wherein in step 2-3, the kernel sizes of the two layers of one-dimensional frequency-domain convolutions are [(6×1), (7×1)], [(7×1), (11×1)], and [(15×1), (15×1)], respectively.

14. The task-independent brainprint recognition apparatus according to claim 9, wherein in step 2-3, the kernel sizes of the one layer of one-dimensional frequency-domain convolution are (12×1), (18×1), and (30×1), respectively.

15. The task-independent brainprint recognition apparatus according to claim 9, wherein the loss functions (16) and (17) are optimized by gradient back propagation.

16. A non-transitory computer-readable storage medium, storing a computer program, wherein the computer program, when executed in a computer, causes the computer to perform the task-independent brainprint recognition method based on feature disentanglement by decorrelation according to claim 1.

17. The non-transitory computer-readable storage medium according to claim 16, wherein step 1 specifically comprises:

step 1-1, downsampling EEG data to 250 Hz, and filtering the original EEG data at 0 to 75 Hz using a Butterworth filter;

step 1-2, performing short-time Fourier transform on the EEG data x processed in step 1-1 to extract time-frequency features;

step 1-3, intercepting the time-frequency features obtained in step 1-2 using a time window, adding to each time-frequency feature a tag of a subject to which the time-frequency feature belongs and a corresponding task tag; and step 1-4, using one task of EEG sample data obtained in step 1-3 as a test set $\{X_t, Y_t, Y_{tl}\}$, and proportionally dividing remaining samples into a training set $$\{X_{sj}, Y_{sj}, Y_{slj}\}_{j=1}^{K}$$

and a validation set $\{X_v, Y_v, Y_{vl}\}$, wherein X, Y, $Y_l$, and K represent a sample, an identity tag, a task tag, and a number of tasks, respectively.

18. The non-transitory computer-readable storage medium according to claim 17, wherein step 1-2 specifically comprises:

using a time-limited window function h(t), assuming that a non-stationary signal x is stationary within one time window, performing piecewise analysis on the signal x by moving of the window function h(t) on a time axis to obtain a set of local "frequency spectra" of the signal, and defining a short-time Fourier transform of signal x($\tau$) as:

$$STFT(t, f) = \int_{-\infty}^{\infty} x(\tau)h(\tau - t)e^{-j2\pi f\tau}d\tau \tag{1}$$

wherein STFT(t,f) represents the short-time Fourier transform of the signal x($\tau$) in time t and frequency f, and h($\tau$−t) represents the window function.

19. The non-transitory computer-readable storage medium according to claim 16, wherein in step 2-1, the low frequency band is 1 to 12 Hz, and the high frequency band is 12 to 30 Hz.

20. A computing device, comprising a memory and a processor, wherein an executable code is stored in the memory, and the processor, when executing the executable code, performs the task-independent brainprint recognition method based on feature disentanglement by decorrelation according to claim 1.

\*    \*    \*    \*    \*